(12) United States Patent
Dargazanli et al.

(10) Patent No.: US 7,700,585 B2
(45) Date of Patent: *Apr. 20, 2010

(54) DERIVATIVES OF N-[PHENYL (PYRROLIDINE-2-YL)METHYL] BENZAMIDE AND N-[(AZEPAN-2-YL) PHENYLMETHYL]BENZAMIDE, PREPARATION METHOD THEREOF AND APPLICATION OF SAME IN THERAPEUTICS

(75) Inventors: Gihad Dargazanli, Cachan (FR); Genevieve Estenne-Bouhtou, Chevilly-Larue (FR); Florence Medaisko, Saint Maur des Fosses (FR); Nathalie Rakotoarisoa, Longiumeau (FR)

(73) Assignee: sanofi-aventis, Paris (FR)

( * ) Notice: Subject to any disclaimer, the term of this patent is extended or adjusted under 35 U.S.C. 154(b) by 124 days.

This patent is subject to a terminal disclaimer.

(21) Appl. No.: 11/741,803

(22) Filed: Apr. 30, 2007

(65) Prior Publication Data

US 2007/0208006 A1  Sep. 6, 2007

Related U.S. Application Data

(60) Division of application No. 11/405,191, filed on Apr. 17, 2006, now Pat. No. 7,226,917, which is a continuation of application No. PCT/FR2004/002644, filed on Oct. 15, 2004.

(30) Foreign Application Priority Data

Oct. 17, 2003 (FR) .................................. 03 12143

(51) Int. Cl.
A61K 31/55 (2006.01)
A61K 31/4025 (2006.01)
C07D 233/04 (2006.01)
C07D 207/20 (2006.01)

(52) U.S. Cl. .................. 514/217.12; 514/428; 540/611; 540/612; 548/578; 548/579

(58) Field of Classification Search ................. 540/611, 540/612; 548/578, 579; 514/217.2, 428
See application file for complete search history.

(56) References Cited

U.S. PATENT DOCUMENTS 7,226,917 B2 * 6/2007 Dargazanli et al. ..... 514/217.12
2006/0223802 A1   10/2006 Dargazanli et al.

FOREIGN PATENT DOCUMENTS

| WO | WO 99/45011   | 9/1999 |
|----|---------------|--------|
| WO | WO 2004/013101 | 2/2004 |
| WO | WO2004013101  | * 2/2004 |
| WO | WO 2006/110724 | 10/2006 |
| WO | WO2006110724  | * 10/2006 |

OTHER PUBLICATIONS

Sahley, Social anxiety and phobia, Pain and Stress publication, 2001, pp. 1-3.*
Gurwitz, Drug Discovery Today, vol. 6, No. 22, Nov. 21, p. 1-2.*
Depondt, Pharmacogenetics in Epilepsy Treatment, Personalized medicine, 2008 p. 1.*
Thomas et al, Human Molecular Genetics, 2007, vol. 16, review issue 2, R183-R194.*
Bergeron et al. Proc. Natl. Acad. Sci. USA, 1998, 95, p. 15730-15734.*
Kinney et al. Journal of Neuroscience, 2003, 23(20), p. 7586-7591.*
Lechner, Current Opinion in Pharmacology, 2006, 6, p. 75-81.*
Leonetti et al Neuroscience, 2006, 137, p. 555-564.*
Bergerone, R., et. al., Modulation of N-Methyl-D-Aspartate Receptor Function by Glycine Transport, Proc. Natl. Acad. Sci. USA, vol. 95, pp. 15730-15734 (1998).

(Continued)

*Primary Examiner*—Ardin Marschel
*Assistant Examiner*—Savitha Rao
(74) *Attorney, Agent, or Firm*—Kelly L. Bender; Balaram Gupta

(57) ABSTRACT

Compounds of formula (I) as defined herein:

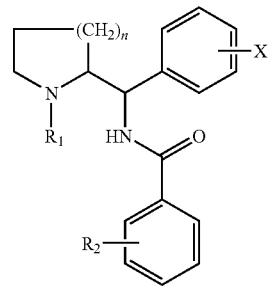

are useful for treating behavioral disorders associated with dementia, psychoses, in particular schizophrenia (deficient form and productive form) and acute or chronic extrapyramidal symptoms induced by neuroleptics; for the treatment of various forms of anxiety, panic attacks, phobias, and compulsive obsessive disorders; for treating various forms of depression, including psychotic depression; for treating disorders caused by alcohol abuse or weaning from alcohol, sexual behavior disorders, eating disorders and for treating migraine. Moreover, the compounds of the invention may be used for treating painful muscle contracture in rheumatology and in acute spinal pathology; for treating spastic contractures of medullary or cerebral origin; for the symptomatic treatment of acute and subacute pain of light to moderate intensity; for treating intense and/or chronic pain, neurogenic pain and intractable pain; for treating Parkinson's disease and Parkinson-like symptoms of neurodegenerative origin or induced by neuroleptics; for treating partial primary and secondary generalized epilepsy of simple or complex symptomology, mixed forms and other epileptic syndromes in addition to another antiepileptic treatment, or in monotherapy, for the treatment of sleep apnea, and for neuroprotection.

4 Claims, No Drawings

OTHER PUBLICATIONS

Depoortere, R., et. al., Neurochemical, Electrophysiological and Pharmacological Profiles of the Selective Inhibitor of the Glycine Transporter-ISSR504734, a Potential New Type of Antipsychotic, Neuropsychopharmacology (2005) vol. 30, pp. 1963-1985.

Kinney, G.G., et. al., The Glycine Transporter Type 1 Inhibitor N-[3-(4'-Fluorophenyl)-3-(4'-Phenylphenoxy)Propyl] Sarcosine Potentiates NMDA Receptor-Mediated Responses in Vivo and Produces an Antipsychotic Profile in Rodent Behavior, The Journal of Neuroscience (2003) vol. 23, No. 20, pp. 7586-7591.

Lechner, S.M., et. al., Glutamate-Based Therapeutic Approaches: Inhibitors of Glycine Transport, Current Opinion in Pharmacology (2005) vol. 6, pp. 75-81.

Leonetti, M., et al., 2-Chloro-N-[(S)-Phenyl [(2S)-Piperidin-2-YL] Methyl]-3-Trifluoromethyl Benzamide, Monohydrochloride, an inhibitor of the Glycine Transporter Type 1, Increases Evoked-Dopamine Release in the Rat Nucleus Accumbens In Vivo Via an Enhanced Glutamatergic Neurotransmission, Neuroscience, vol. 137, (2006) pp. 555-564.

Dargazanli et al, Notice of Allowability issued Feb. 2, 2007 for U.S. Appl. No. 11/405,191, pp. 1-11.

Sur, et al., Glycine Transporter I Inhibitors and Modulation of NMDA Receptor-Mediated Excitatory Neurotransmission, Current Drug Targets, (2007), vol. 8, pp. 643-649.

\* cited by examiner

DERIVATIVES OF N-[PHENYL (PYRROLIDINE-2-YL)METHYL] BENZAMIDE AND N-[(AZEPAN-2-YL) PHENYLMETHYL]BENZAMIDE, PREPARATION METHOD THEREOF AND APPLICATION OF SAME IN THERAPEUTICS

CROSS-REFERENCE TO RELATED APPLICATIONS

This application is a divisional of 11/405,191, filed Apr. 17, 2006 now U.S. Pat. No. 7,226,917, which is a continuation of International application No. PCT/FR2004/002644, filed Oct. 15, 2004, both of which are incorporated herein by reference in their entirety, which claims priority from French Patent Application No. 0312143, filed Oct. 17, 2003.

SUMMARY OF THE INVENTION

The present invention relates to compounds corresponding to the general formula (I)

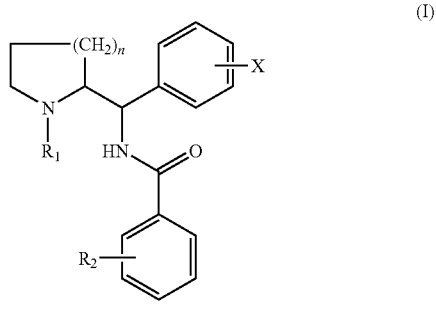

(I)

in which
n represents the number 1 or 3,
$R_1$ represents either a hydrogen atom, a linear or branched ($C_1$-$C_7$)alkyl group optionally substituted with one or more fluorine atoms, a ($C_3$-$C_7$)cycloalkyl group, a ($C_3$-$C_7$)cycloalkyl($C_1$-$C_3$)alkyl group, a phenyl($C_1$-$C_3$)alkyl group optionally substituted with one or two methoxy groups, a ($C_2$-$C_4$)alkenyl group, or a ($C_2$-$C_4$)alkynyl group,
X represents either a hydrogen atom or one or more substituents chosen from halogen atoms and trifluoromethyl and linear or branched ($C_1$-$C_6$)alkyl and ($C_1$-$C_6$)alkoxy groups,
$R_2$ represents either a hydrogen atom or one or more substituents chosen from halogen atoms and trifluoromethyl, linear or branched ($C_1$-$C_6$)alkyl and ($C_1$-$C_6$)-alkoxy, ($C_3$-$C_7$)cycloalkyl, phenyl, cyano, acetyl, benzoyl, S($C_1$-$C_6$)alkyl, ($C_1$-$C_6$)alkylsulfonyl, carboxyl and ($C_1$-$C_6$)alkoxycarbonyl groups, or a group of general formula $NR_3R_4$, $SO_2NR_3R_4$ or $CONR_3R_4$, in which $R_3$ and $R_4$ represent, independently of each other, a hydrogen atom or a linear or branched ($C_1$-$C_6$)alkyl or ($C_3$-$C_7$)cycloalkyl group, or form, with the nitrogen atom that bears them, a pyrrolidine, piperidine or morpholine ring.

BACKGROUND OF THE INVENTION

Compounds of structure similar to that of the compounds of the invention are described in patent U.S. Pat. No. 5,254, 569 as analgesics, diuretics, anticonvulsivants, anesthetics, sedatives and cerebroprotective agents, via a mechanism of action on the opiate receptors. Other compounds of similar structure are described in patent application EP-0 499 995 as 5-$HT_3$ antagonists that are useful in the treatment of psychotic disorders, neurological diseases, gastric symptoms, nausea and vomiting.

DETAILED DESCRIPTION OF THE INVENTION

The compounds of general formula (I) may exist in the form of threo(1R,2R; 1S,2S) or erythro(1S,2R; 1R,2S) racemates or in the form of enantiomers; they may exist in the form of free bases or of acid-addition salts.

Compounds of structure similar to that of the compounds of the invention are described in patent U.S. Pat. No. 5,254, 569 as analgesics, diuretics, anticonvulsivants, anesthetics, sedatives and cerebroprotective agents, via a mechanism of action on the opiate receptors. The compounds of the invention show particular activity as specific inhibitors of the glycine transporters glyt1 and/or glyt2.

The compounds of general formula (I) in which $R_1$ is other than a hydrogen atom may be prepared via a process illustrated by scheme 1 below.

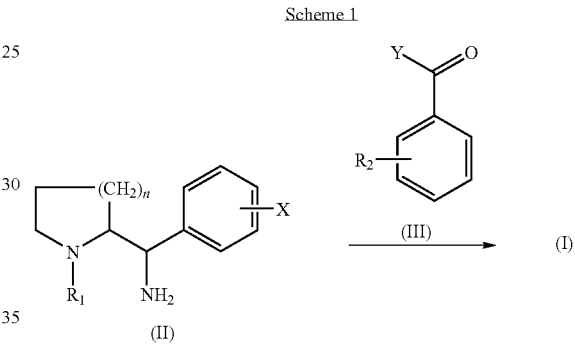

Scheme 1

Coupling of a diamine of general formula (II) of threo or erythro relative configuration or as a mixture, in which $R_1$ and X are as defined above (with $R_1$ other than a hydrogen atom) is performed with an activated acid or an acid chloride of general formula (III) in which Y represents an electrophilic group, such as a halogen atom, and $R_2$ is as defined above, using the methods known to those skilled in the art.

The pure erythro or threo compounds of general formula (I) may be obtained according to any method known to those skilled in the art, for example by separation by high-performance liquid chromatography.

For n=1 with $R_1$ other than a hydrogen atom and X as defined above, the diamine of general formula (II), of threo or erythro relative configuration or as a mixture, may be prepared via the process illustrated by scheme 2 route A.

The ketone IV in which P represents Boc may be reduced to the erythro/threo alcohol (X), the ratio of which depends on the nature of the hydride used, according to a method described in J.Chem. Soc. Chem. Commun., 1986, 412-413. The protecting group is then removed according to a standard method, in a mixture of dichloromethane and trifluoroacetic acid. The amino alcohol (XI) is thus obtained, on which an N-alkylation is then performed using a halogenated derivative of formula $R_1Z$ and a base such as potassium carbonate to give the functionalized amino alcohol of general formula (XII).

Finally, under standard Mitsunobu conditions, according to a method described in Bull. Soc. Chim. Belg. (106), 1997, 77-84 in the presence of hydrazoic acid and triphenylphosphine, the diamine of general formula (II) is obtained.

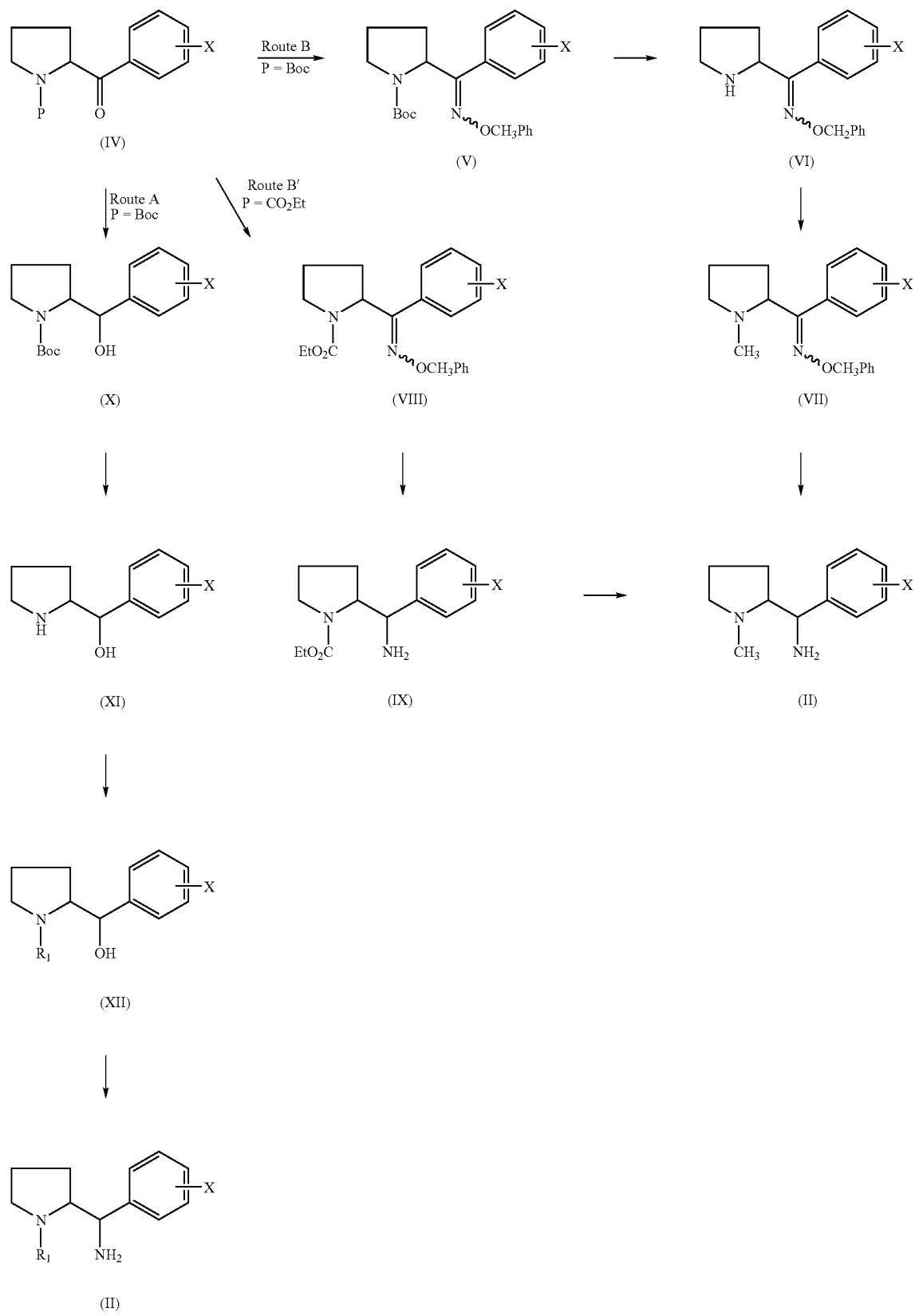

For n=1 with $R_1$=$CH_3$ and X as defined above, the diamine of general formula (II), of threo or erythro relative configuration or as a mixture, may also be obtained according to routes B and B' of scheme 2 and according to scheme 3.

According to route B, the ketone (IV) in which X is as defined above is reacted with benzylhydroxylamine hydrochloride in refluxing pyridine to give a mixture of oxime (V) that is deprotected with trifluoroacetic acid to obtain the free amine (VI).

Methylation of the pyrrolidine is performed conventionally in refluxing formaldehyde and formic acid to generate the compound (VII). Finally, hydrogenation of this compound, catalyzed with palladium-on-charcoal, in an alcoholic solvent in the presence of aqueous hydrochloric acid leads to the diamine of general formula (II).

According to route B', the ketone of general formula (IV) in which P represents $CO_2Et$ and X is as defined above is reacted with benzylhydroxylamine hydrochloride in refluxing ethanol to give a mixture of oximes (VIII), on which is performed a hydrogenation catalyzed with palladium-on-charcoal in an alcoholic solvent in the presence of aqueous hydrochloric acid, to give the carbamate (IX). Reduction of the carbamate of general formula (IX) with lithium aluminum hydride in a refluxing solvent such as ether gives the diamine of general formula (II).

According to scheme 3, the amino alcohol (XIII) is converted into the azide (XIV) under the standard Mitsunobu conditions, according to a method described in J. Org. Chem., (64), 1999, 6106-6111. Reduction of the azide carbamate (XIV) with lithium aluminum hydride in a refluxing solvent such as tetrahydrofuran gives a mixture of diamines of general formula (II).

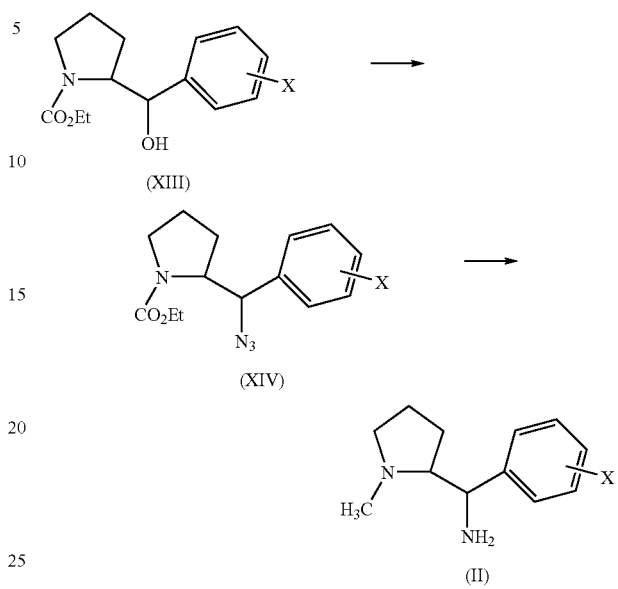

The diamine of general formula (II) of threo or erythro relative configuration in which $R_1$ is other than a hydrogen atom and n=3 may be prepared via a process illustrated by scheme 4 below.

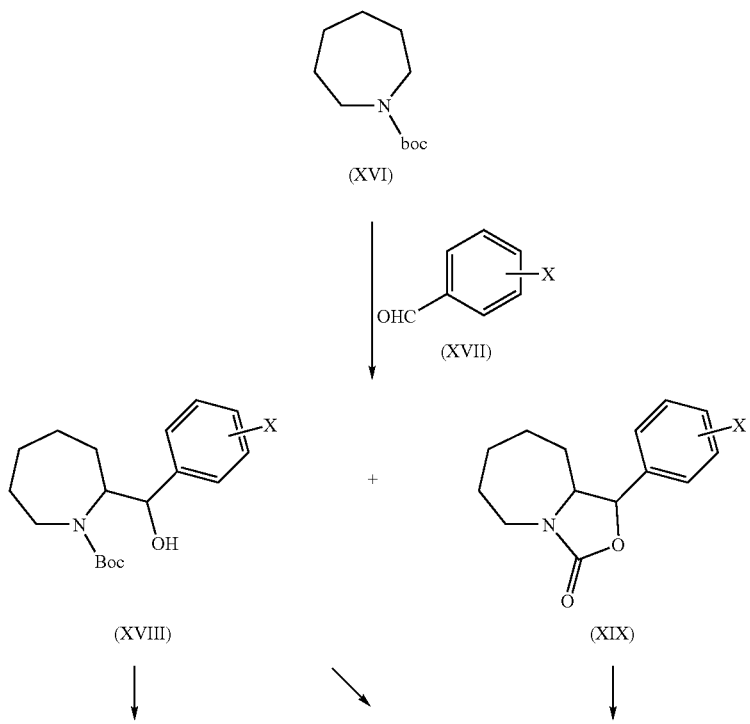

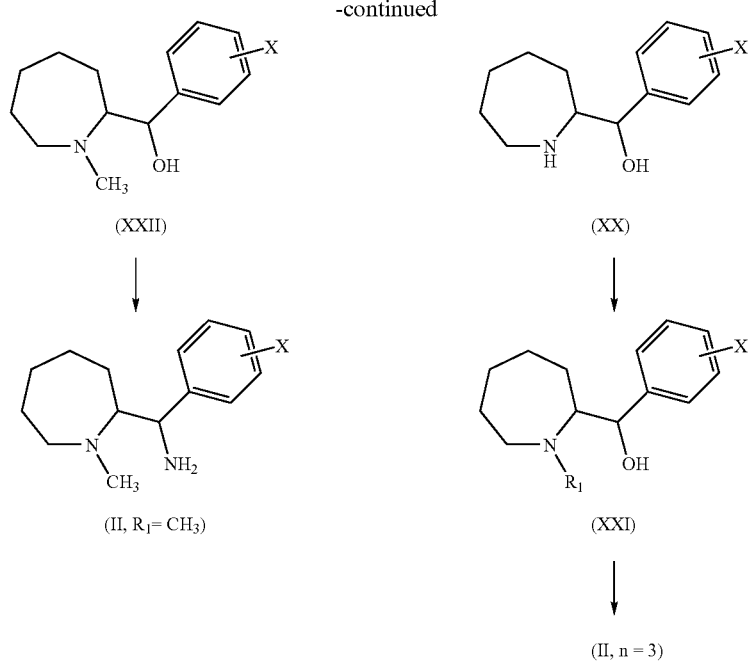

α-Lithiation of the azepane of general formula (XVI) in which Boc represents a 1,1-dimethylethoxycarbonyl group, is performed with sec-butyllithium in the presence of TMEDA (N,N,N',N'-tetramethylethylenediamine) in an ether solvent such as diethyl ether at −78° C., to react the lithioamine formed in situ with the benzaldehyde of general formula (XVII) according to a method described in J. Org. Chem., (58), 5, 1993, 1109-1117. A mixture of alcohol of general formula (XVIII) of erythro configuration and of cyclic carbamate of general formula (XIX) of threo configuration may thus be obtained.

The carbamate of general formula (XVIII) of erythro configuration may then be reduced to the erythro N-methylamino alcohol of general formula (XXII) via the action of a mixed hydride such as lithium aluminum hydride, in an ether solvent such as tetrahydrofuran, between room temperature and the reflux temperature. The erythro alcohol of general formula (XXII) is then converted into the erythro intermediate of general formula (II) in which $R_1$ represents a methyl group, in two steps: the alcohol function is first converted into an electrophilic group, for example a methanesulfonate group, via the action of mesyl chloride, in a chlorinated solvent such as dichloromethane, and in the presence of a base such as triethylamine, between 0° C. and room temperature, and the electrophilic group is then reacted with liquefied ammonia at −50° C., in an alcohol such as ethanol, in a closed medium such as an autoclave, between −50° C. and room temperature.

The carbamate of general formula (XVIII) of erythro configuration may also be deprotected using a strong base such as aqueous potassium hydroxide, in an alcohol such as methanol, to obtain the corresponding amino alcohol of general formula (XX). Under the same hydrolysis conditions, the threo cyclic carbamate of general formula (XIX) gives the threo amino alcohol of general formula (XX).

An N-alkylation is then performed using a halogenated derivative of formula $R_1Z$, in which $R_1$ is as defined above, but other than a hydrogen atom, and Z represents a halogen atom, in the presence of a base such as potassium carbonate, in a polar solvent such as N,N-dimethylformamide, between room temperature and 100° C., to give the alkylated derivative of general formula (XXI). This derivative is then treated as described with respect to the alcohol of general formula (XXII).

The compounds of general formula (I) in which $R_1$ represents a hydrogen atom may be prepared from a compound of general formula (I) in which $R_1$ represents either an optionally substituted phenylmethyl group, and in deprotecting the nitrogen of the piperidine ring, for example with an oxidizing agent or with a Lewis acid such as boron tribromide or via hydrogenolysis, or an alkenyl group, preferably allyl, followed by deprotection with a $Pd^0$ complex to give a compound of general formula (I) in which $R_1$ represents a hydrogen atom.

Moreover, the chiral compounds of general formula (I) may also be obtained either by separating the racemic compounds by high-performance liquid chromatography (HLPC) on a chiral column, or by starting with the chiral amine obtained either by resolving the racemic amine of general formula (II) by using a chiral acid, such as tartaric acid, camphorsulfonic acid, dibenzoyltartaric acid or N-acetylleucine, by fractional and preferential recrystallization of a diastereoisomeric salt in a solvent of alcohol type, or via chiral synthesis according to route B' or A starting with the chiral ketone of general formula (IV) of scheme 2, or alternatively starting with the chiral alcohol of general formula (XIII) of scheme 3.

The racemic ketone of general formula (IV) may be prepared according to a method described in Tetrahedron Lett., (38) (5), 1997, 783-786; Tetrahedron, (59), 2003, 1083-1094. In the chiral series, the ketone of general formula (IV) or the chiral alcohols of general formulae (X) and (XIII) may be prepared according to a method described in international patent application WO 03/004 468 and in J. Chem. Soc. Perkins Trans I, 1987, 1465-1471. The perhydroazepine of general formula (XVI) may be prepared according to a method described in J. Org. Chem., (58), 5, 1993, 1109-1117.

The examples that follow illustrate the preparation of a number of compounds of the invention. The elemental microanalyses and the IR and NMR spectra and the HPLC on a chiral column confirm the structures and the enantiomeric purities of the compounds obtained.

The numbers indicated in parentheses in the titles of the examples correspond to those in the first column of the table given later.

In the compound names, the hyphen "-" forms part of the word, and the underscore mark "_" serves merely to indicate the line break; it should be omitted if a line break does not occur at that point, and should not be replaced either with a normal hyphen or with a space.

EXAMPLE 1

(Compound 1)

Threo-2-chloro-N-[(1-methyl-2-pyrrolidinyl)phenyl_methyl]-3-trifluoromethylbenzamide hydrochloride 1:1

1.1. tert-Butyl 2-[[(benzyloxy)imino](phenyl)me_thyl]-1-pyrrolidinecarboxylate 8.8 g (31.36 mmol) of tert-butyl 2-benzoylpyrrolidine-1-carboxylate and 5.6 g (35.15 mmol) of benzylhydroxylamine hydrochloride dissolved in 100 ml of absolute ethanol and 35 ml of 1M sodium hydroxide are introduced into a 1000 ml round-bottomed flask equipped with a magnetic stirrer, and the mixture is refluxed for 16 hours.

After evaporating the reaction medium to dryness under reduced pressure, the residue is diluted with water and dichloromethane, and the aqueous phase is separated out and extracted with dichloromethane. After washing the combined organic phases, drying over sodium sulfate and evaporating off the solvent under reduced pressure, the residue is purified by column chromatography on silica gel, eluting with a mixture of ethyl acetate and cyclohexane.

8 grams of product are thus obtained in the form of an oil.

1.2. Phenyl(2-pyrrolidinyl)methanone O-benzyloxime 8 g (20 mmol) of tert-butyl 2-[[(benzoyloxy)imino](phenyl)methyl]-1-pyrrolidinecarboxylate dissolved in 400 ml of a mixture of 30% trifluoroacetic acid in dichloromethane are introduced into a 500 ml round-bottomed flask equipped with a magnetic stirrer, and the mixture is stirred for 4 hours at room temperature. After evaporating the reaction medium to dryness under reduced pressure, the residue is diluted with aqueous ammonia and dichloromethane, and the aqueous phase is separated out and extracted with dichloromethane. After washing the combined organic phases, drying over sodium sulfate and evaporating the solvent under reduced pressure, the residue is purified by column chromatography on silica gel, eluting with a mixture of dichloromethane and methanol.

4 g of product are obtained.

1.3. (1-Methyl-2-pyrrolidinyl)(phenyl)methanone O-benzyloxime 1.2 g (4.28 mmol) of phenyl(2-pyrrolidinyl)methanone O-benzyloxime in 4 ml of a mixture (1/1) of formic acid and aqueous 37% formaldehyde are introduced into a 50 ml round-bottomed flask equipped with a magnetic stirrer, and the mixture is refluxed for 16 hours.

After evaporating the reaction medium to dryness under reduced pressure, the residue is diluted with aqueous ammonia and dichloromethane, and the aqueous phase is separated out and extracted with dichloromethane. After washing the combined organic phases, drying over sodium sulfate and evaporating off the solvent under reduced pressure, the residue is purified by column chromatography on silica gel, eluting with a mixture of dichloromethane and methanol.

1.05 g of product are obtained.

1.4. [(1-Methyl-2-pyrrolidinyl)phenyl)methylamine 1.05 g (3.56 mmol) of (1-methyl-2-pyrrolidinyl)(phenyl)methanone O-benzyloxime dissolved in a mixture of 20 ml of ethanol and 10 ml of 1N hydrochloric acid in the presence of a spatula-tip of 10% palladium-on-charcoal are placed in a Parr flask under a nitrogen atmosphere. The reagents are placed under a hydrogen atmosphere and stirred for 8 hours.

After filtering off the catalyst and evaporating the filtrate under reduced pressure, the residue is diluted with aqueous ammonia and dichloromethane, and the aqueous phase is separated out and extracted with dichloromethane. After washing the combined organic phases, drying over sodium sulfate and evaporating off the solvent under reduced pressure, 0.54 g of product is thus obtained in the form of an oil, which is used in crude form in the following step.

1.5. Threo-2-chloro-N-[(1-methyl-2-methylpyrrolidi_nyl)phenylmethyl]-3-trifluoromethylbenzamide hydrochloride 1:1

0.54 g (2.84 mmol) of [(1-methyl-2-pyrrolidinyl)phenyl) methylamine and 0.41 g of potassium carbonate dissolved in 7 ml of dichloromethane at 0° C. are placed in a 100 ml round-bottomed flask under a nitrogen atmosphere. A solution of 0.72 g (2.97 mmol) of 2-chloro-3-trifluoromethylbenzoyl chloride dissolved in 3 ml of dichloromethane is added and the mixture is left for 16 hours at room temperature.

The reaction mixture is diluted with water and dichloromethane, and the aqueous phase is separated out and extracted with dichloromethane. After washing the combined organic phases, drying over sodium sulfate and evaporating off the solvent under reduced pressure, the residue is purified by column chromatography on silica gel, eluting with a mixture of dichloromethane and methanol.

110 mg of threo-2-chloro-N-[(1-methyl-2-pyrrolidinyl) phenylmethyl]-3-trifluoromethylbenzamide are thus isolated.

This product is dissolved in a few ml of 2-propanol, 6 ml of a 0.1N solution of hydrogen chloride in 2-propanol are added and the mixture is concentrated under reduced pressure in order to reduce the volume of the solvent. After trituration, 0.10 g of hydrochloride is finally isolated in the form of a solid.

Melting point: 96-110° C.

EXAMPLE 2

(Compound 2)

Threo-4-amino-3,5-dichloro-N-[(1-methyl-2-pyrrolidinyl)phenylmethyl)-benzamide hydrochloride 1:1

0.975 g (4.73 mmol) of 4-amino-3,5-dichlorobenzoic acid, 0.639 g (4.73 mmol) of hydroxybenzotriazole and 0.906 g (4.73 mmol) of 1-[3-(dimethylamino)propyl]-3-ethylcarbodiimide hydrochloride dissolved in 50 ml of dichloromethane are introduced into a 100 ml round-bottomed flask equipped with a magnetic stirrer. The mixture is left at room temperature for 30 minutes, 0.9 g (4.73 mmol) of [(1-methyl-2-pyrrolidinyl)phenyl)methyl]amine dissolved in 20 ml of dichloromethane is added and the mixture is left at room temperature overnight.

After hydrolyzing with water and diluting with dichloromethane, the aqueous phase is separated out and is extracted with dichloromethane. After washing the combined organic phases, drying over sodium sulfate and evaporating off the solvent under reduced pressure, the residue is purified by column chromatography on silica gel, eluting with a mixture of dichloromethane and methanol.

0.19 g of oily product is obtained.

This product is dissolved in a few ml of 2-propanol, 20 ml of a 0.1N solution of hydrogen chloride in 2-propanol are added, and the mixture is concentrated under reduced pressure in order to reduce the volume of the solvent. After trituration, 0.19 g of hydrochloride is finally isolated in the form of a solid.

Melting point: 155-162° C.

EXAMPLE 3

(Compound 3)

Threo-N-[(1-allyl-2-pyrrolidinyl)phenylmethyl]-2-chloro-3-trifluoromethylbenzamide 1:1

3.1. tert-Butyl erythro-2-[hydroxy(phenylmethyl]-1-pyrrolidinecarboxylate 3 g (10.89 mmol) of tert-butyl 2-benzoyl-1-pyrrolidinecarboxylate dissolved in 110 ml of tetrahydrofuran at −70° C. are placed in a 250 ml three-necked flask equipped with a magnetic stirrer, under a nitrogen atmosphere. 29 ml (43.58 mmol) of a 1.5M solution of diisobutylaluminum hydride in toluene are added dropwise. The mixture is left for 2 hours at −70° C. and the temperature is allowed to rise to −20° C. The mixture is then hydrolyzed cautiously with 50 ml of methanol. After evaporating the reaction mixture under reduced pressure, the residue is diluted with 1N hydrochloric acid and dichloromethane, and the aqueous phase is separated out and extracted with dichloromethane. After washing the combined organic phases, drying over sodium sulfate and evaporating off the solvent under reduced pressure, 2.8 g of a mixture mainly containing the tert-butyl erythro-2-[hydroxy(phenylmethyl]-1-pyn-olidinecarboxylate diastereoisomer are obtained, which product is used in crude form in the following step.

3.2. Erythro-phenyl(2-pyrrolidinyl)methanol trifluoroacetate 5 g (21.99 mmol) of tert-butyl erythro-2-[hydroxy(phenylmethyl]-1-pyrrolidinecarboxylate dissolved in a mixture of 75 ml of dichloromethane and 30 ml of trifluoroacetic acid are placed in a 250 ml round-bottomed flask equipped with a magnetic stirrer, and the mixture is stirred. It is left at room temperature for 2 hours.

The reaction mixture is evaporated under reduced pressure. 5 g of a mixture containing erythro-phenyl(2-pyrrolidinyl)methanol trifluoroacetate are thus obtained, which product is used in crude form in the following step.

3.3. Erythro-(1-allyl-2-pyrrolidinyl)phenyl)methanol 5 g (17.16 mmol) of erythro-phenyl(2-pyrrolidinyl)methanol trifluoroacetate, 5.9 g (43 mmol) of potassium carbonate and 1.8 ml (20.6 mmol) of allyl bromide dissolved in 50 ml of acetonitrile are placed in a 250 ml round-bottomed flask equipped with a magnetic stirrer, and the mixture is stirred at room temperature for 16 hours.

After evaporating the reaction medium to dryness under reduced pressure, the residue is diluted with aqueous ammonia and dichloromethane, and the aqueous phase is separated out and extracted with dichloromethane. After washing the combined organic phases, drying over sodium sulfate and evaporating off the solvent under reduced pressure, the residue is purified by column chromatography on silica gel, eluting with a mixture of dichloromethane and methanol.

1.1 g of a mixture containing erythro-(1-allyl-2-pyrrolidinyl)phenyl)methanol are thus obtained.

3.4. Erythro-[(1-allyl-2-pyrrolidinyl)phenyl)methyl]amine.

1.1 g (5.06 mmol) of erythro-1-(allyl-2-pyrrolidinyl)phenyl)methanol and 1.6 g (6.07 mmol) of triphenylphosphine dissolved in 15 ml of tetrahydrofuran are introduced into a 100 ml three-necked flask equipped with a magnetic stirrer, under a nitrogen atmosphere. 6 ml of a 1M solution of hydrazoic acid in benzene (6 mmol) are added. A solution of 1.09 ml (0.56 mmol) of diisopropylcarbodiimide in 10 ml of tetrahydrofuran is added dropwise to this solution. The mixture is heated at 40° C. for 16 hours, 1.3 g (5.06 mmol) of triphenylphosphine are then added, the mixture is stirred for 30 minutes, 0.6 ml of water is then added and stirring is continued for 6 hours.

The resulting mixture is hydrolyzed with 1N hydrochloric acid and diluted with chloroform. The aqueous phase is basified with aqueous ammonia and extracted several times with chloroform. After washing the combined organic phases, drying over sodium sulfate and evaporating off the solvent under reduced pressure, 1 g of an orange-colored oil containing threo-[(1-allyl-2-pyrrolidinyl)phenyl)methyl]amine is obtained, which product is used in crude form in the following step.

3.5. Threo-N-[(1-allyl-2-pyrrolidinyl)phenylmethyl]-2-chloro-3-trifluoromethylbenzamide According to the procedure described in Example 1.5, starting with 1 g (4.62 mmol) of threo-[(1-allyl-2-pyrrolidinyl)phenyl)methyl]amine, 1.13 g (4.62 mmol) of 2-chloro-3-trifluoromethylbenzoyl chloride and 0.64 g (4.62 mmol) of potassium carbonate, 20 mg of an oil that crystallizes are obtained.

Melting point: 117-123° C.

EXAMPLE 4

(Compound 4)

3-(Aminosulfonyl)-4-chloro-N-[(S)-[(2S)-1-methyl-2-pyrrolidinyl] (phenyl)methyl]benzamide hydrochloride 1:1

4.1. Ethyl 2-[(benzyloxy)imino]phenylmethyl-1-pyrrolidinecarboxylate 1.36 g (5.5 mmol) of ethyl 2-benzoyl-1-pyrrolidinecarboxylate dissolved in 30 ml of ethanol are introduced into a 100 ml round-bottomed flask equipped with a magnetic stirrer, 1.75 g (10.96 mmol) of benzylhydroxylamine hydrochloride are added and the mixture is refluxed for 12 hours. After evaporating off the solvent under reduced pressure, the residue is taken up in ethyl acetate and the organic phase is washed with saturated sodium chloride solution, dried over sodium sulfate and evaporated under reduced pressure. 1.95 g of a yellow oil are obtained, which product is purified by column chromatography on silica gel, eluting with a mixture of ethyl acetate and cyclohexane.

1.56 g of product are obtained.

4.2. Ethyl (S)-2-[(S)-amino(phenyl)methyl]-1-pyrrolidinecarboxylate and ethyl [phenyl(2-pyrrolidinyl) methyl]carbamate 1.56 g (4.43 mmol) of ethyl [(benzoyloxy)imino]phenylmethyl-1-pyrrolidine-carboxylate are introduced into 40 ml of ethanol and 8 ml of 1N hydrochloric acid in a 250 ml Parr flask, 0.15 g of 10% palladium-on-charcoal is added and the mixture is placed under a hydrogen atmosphere for 7 hours.

After filtering off the catalyst and evaporating the filtrate under reduced pressure, the residue is diluted with aqueous ammonia and dichloromethane, and the aqueous phase is separated out and extracted with dichloromethane. After washing the combined organic phases, drying over sodium sulfate and evaporating the solvent under reduced pressure, 1 g of a mixture comprising ethyl (S)-2-[(S)-amino(phenyl) methyl]-1-pyrrolidinecarboxylate and ethyl [phenyl(2-pyrrolidinyl)-methyl]carbamate is obtained, which product is used in crude form in the following step.

4.3. [(S)-[(2S)-(1-Methyl-2-pyrrolidinyl)]phenylmethyl]amine 1 g (4 mmol) of the mixture comprising ethyl (S)-2-[(S)-amino(phenyl)methyl]-1-pyrrolidinecarboxylate and ethyl [phenyl(2-pyrrolidinyl)methyl]carbamate dissolved in 20 ml of anhydrous ether at 0° C. is introduced into a 100 ml round-bottomed flask equipped with a magnetic stirrer, under a nitrogen atmosphere. 0.8 g (21 mol) of lithium aluminum hydride is added portionwise and the mixture is refluxed for 5 hours.

After cooling, the mixture is successively treated with 0.8 ml of water, 0.8 ml of 15% sodium hydroxide and 2.4 ml of water.

After filtering through Celite®, the filtrate is concentrated under reduced pressure.

The residue obtained (0.7 g) is purified by column chromatography on silica gel, eluting with a mixture of dichloromethane, methanol and aqueous ammonia. 0.12 g of product is obtained in the form of a yellow oil.

4.4. 3-(Aminosulfonyl)-4-chloro-N-[(S)-[(2S)-1-methyl-2-pyrrolidinyl](phenyl)methyl]benzamide hydrochloride 1:1

According to the procedure described in Example 2, starting with 0.12 g (0.63 mmol) of [(S)-[(2S)-(1-methyl-2-pyrrolidinyl)]phenylmethyl]amine, 0.12 g (0.63 mmol) of 1-[3-(dimethylamino)propyl]-3-ethylcarbodiimide hydrochloride, 0.085 g (0.63 mmol) of hydroxybenzotriazole and 0.14 g (0.63 mmol) of 4-chloro-3-sulfonylbenzoic acid, and after work-up and purification by chromatography on silica gel with a gradient of dichloromethane and methanol, 0.12 g of 3-(aminosulfonyl)-4-chloro-N-[(S)-[(2S)-1-methyl-2-pyrrolidinyl](phenyl)methyl]benzamide is obtained.

This product is dissolved in a few ml of 2-propanol, 20 ml of a 0.1N solution of hydrogen chloride in 2-propanol are added and the mixture is concentrated under reduced pressure in order to reduce the volume of the solvent. After trituration, 0.09 g of hydrochloride is finally isolated in the form of a white solid.

Melting point: 165-170° C.

EXAMPLE 5

(Compound 5)

Erythro-4-amino-3-chloro-N-[1-methyl-2-pyrrolidinyl](phenyl)methyl]-5-(trifluoromethyl)benzamide hydrochloride 1:1

5.1. Ethyl erythro-[azido(phenyl)methyl]-1-pyrrolidinecarboxylate 2.9 g (11.6 mmol) of ethyl threo-[hydroxy(phenyl)methyl]-1-pyrrolidinecarboxylate dissolved in 150 ml of tetrahydrofuran at 0° C. are placed in a 500 ml round-bottomed flask equipped with a magnetic stirrer and under an argon atmosphere. 4.57 g (17.4 mmol) of triphenylphosphine and 35 mmol of a solution of hydrazoic acid in toluene are added. 2.74 ml (17.4 mmol) of ethyl azidodicarboxylate are added dropwise and the mixture is stirred for 24 hours.

1N sodium hydroxide is added and the mixture is taken up in ethyl acetate. The organic phase is dried over sodium sulfate and evaporated under reduced pressure. 10 g of a residue are obtained, and are purified by chromatography on silica gel with a gradient of cyclohexane and ethyl acetate. 1.17 g of ethyl erythro-[azido(phenyl)methyl]-1-pyrrolidinecarboxylate are thus obtained.

5.2. Erythro-[(1-methyl-2-pyrrolidinyl)phenyl)methyl]amine 0.8 g (21.32 mmol) of lithium aluminum hydride is placed in 25 ml of tetrahydrofuran in a 100 ml three-necked flask equipped with a magnetic stirrer, under argon, and a solution of 1.17 g (4.26 mmol) of ethyl erythro-[azido(phenyl)methyl]-1-pyrrolidinecarboxylate in 10 ml of tetrahydrofuran is added and the mixture is heated at 70° C. for 2 hours.

After cooling, the mixture is successively treated with 0.8 ml of water, 0.8 ml of 15% sodium hydroxide and 2.4 ml of water.

After filtering through Celite®, the filtrate is evaporated under reduced pressure and the residue is purified by chromatography on silica gel with a mixture of dichloromethane, methanol and aqueous ammonia. 0.16 g of erythro-[(1-methyl-2-pyrrolidinyl)phenyl)methyl]amine and 0.15 g of [methylphenyl(2-pyrrolidinyl)-methyl]amine are thus obtained.

5.3. Erythro-4-amino-3-chloro-N-[1-methyl-2-pyrrolidinyl] (phenyl)methyl]-5-(trifluoromethyl)benzamide hydrochloride 1:1

According to the procedure described in Example 2, starting with 0.073 g (0.38 mmol) of erythro-(1-methyl-2-pyrrolidinyl)]phenyl)methyl]amine, 0.074 g (0.38 mmol) of 1-[3-(dimethylamino)propyl]-3-ethylcarbodiimide hydrochloride, 0.052 g (0.38 mmol) of hydroxybenzotriazole and 0.092 g (0.63 mmol) of 4-amino-3-chloro-5-trifluoromethylbenzoic acid, and after work-up and purification by chromatography on silica gel with a gradient of dichloromethane and methanol, 0.089 g of erythro-4-amino-3-chloro-N-[1-methyl-2-pyrrolidinyl](phenyl)methyl]-5-(trifluoromethyl)benzamide is obtained.

This product is dissolved in a few ml of 2-propanol, 20 ml of a 0.1N solution of hydrogen chloride in 2-propanol are added and the mixture is concentrated under reduced pressure in order to reduce the volume of the solvent. After trituration, 0.07 g of hydrochloride is finally isolated in the form of a white solid.

Melting point: 130-140° C.

EXAMPLE 6

(Compound 6)

3-(Aminosulfonyl)-4-chloro-N-[(R)-[(2S)-1-methyl-2-pyrrolidinyl]-(phenyl)methyl]benzamide hydrochloride 1:1

Using the synthetic method of Example 5, starting with the chiral threo amino alcohol ethyl (2S)-2-[2-(S)-hydroxy(phenyl)methyl]-1-pyrrolidinecarboxylate, 0.12 g of 3-(aminosulfonyl)-4-chloro-N-[(R)-[(2S)-1-methyl-2-pyrrolidinyl](phenyl)methyl]benzamide hydrochloride 1:1 is obtained.

Melting point: 190-192° C.

EXAMPLE 7

(Compound 7)

Erythro-2-chloro-N-[(R)-[(2S)-1-methyl-2-azepanyl](phenyl)methyl]-3-(trifluoromethyl)benzamide hydrochloride 1:1

7.1. tert-Butyl 2-[hydroxy(phenyl)methyl]-1-azepanecarboxylate 5 g (25.09 mmol) of tert-butyl 1-azepanecarboxylate and 3.8 ml (25.09 mmol) of tetramethylenediamine dissolved in 30 ml of anhydrous ether at −75° C. are placed in a 250 ml three-necked flask equipped with a magnetic stirrer, under an argon atmosphere. 21 ml (27.60 mmol) of 1.3M sec-butyl-lithium in cyclohexane are added dropwise. The temperature is allowed to rise to −50° C. over 3 hours (solution A).

3.8 ml (37.63 mmol) of benzaldehyde in 10 ml of anhydrous ether (solution B) are placed in a 250 ml round-bottomed flask equipped with a magnetic stirrer, under an argon atmosphere. The two solutions are cooled to −75° C. and solution A is introduced into solution B while controlling the temperature. At the end of the addition, the mixture is allowed to warm to room temperature and is stirred overnight.

After hydrolyzing with saturated ammonium chloride solution, the aqueous phase is separated out and is extracted with ethyl acetate. After washing the combined organic phases, drying over sodium sulfate and evaporating off the solvent under reduced pressure, the residue (10 g) is purified by column chromatography on silica gel, eluting with a mixture of ethyl acetate and cyclohexane.

2 g of tert-butyl 2-[hydroxy(phenyl)methyl]-1-azepanecarboxylate are thus obtained.

7.2. (1-Methyl-2-azepanyl)phenyl)methanol 1.2 g (32.74 mmol) of lithium aluminum hydride are suspended in 10 ml of tetrahydrofuran in a 100 ml two-necked flask under a nitrogen atmosphere, equipped with a magnetic stirrer and on which is mounted a condenser. A solution of 2 g (6.55 mmol) of tert-butyl 2-[hydroxy(phenyl)methyl]-1-azepanecarboxylate in 10 ml of tetrahydrofuran is added dropwise and the mixture is refluxed for 5 hours.

After cooling, 5.5 ml of a 0.1M solution of potassium sodium tartrate are added and the mixture is stirred at room temperature overnight.

After filtering off the insoluble material under reduced pressure and rinsing with tetrahydrofuran, the filtrate is concentrated under reduced pressure. 1.36 g of an oil are obtained, which product is purified by column chromatography on silica gel, eluting with a mixture of dichloromethane, methanol and aqueous ammonia.

0.95 g of (1-methyl-2-azepanyl)phenyl)methanol is obtained.

7.3. [(1-Methyl-2-azepanyl)phenyl)methyl]amine 0.95 g (4.33 mmol) of (1-methyl-2-azepanyl)phenyl)methanol and 0.6 ml (4.33 mmol) of triethylamine dissolved in 20 ml of dichloromethane at 0° C. are placed in a 100 ml round-bottomed flask under a nitrogen atmosphere, equipped with a magnetic stirrer. 0.34 ml of mesyl chloride is added and the mixture is stirred at room temperature for 3 hours.

After evaporating off the solvents under reduced pressure, the residue is taken up in 20 ml of ethanol and is added to a solution of liquefied ammonia in an autoclave cooled to −50° C. The autoclave is closed and the mixture is stirred at room temperature for 48 hours.

The reaction mixture is diluted with water and dichloromethane. The aqueous phase is extracted 3 times with dichloromethane. After washing the combined organic phases, drying over sodium sulfate and evaporating off the solvent under reduced pressure, 1.7 g of [(1-methyl-2-azepanyl)phenyl)methyl]amine are obtained in the form of an oil, which is used in crude form in the following step.

7.4. Erythro-2-chloro-N-(1-methyl-2-azepanyl)(phenyl)methyl]-3-(trifluoromethyl)benzamide hydrochloride 1:1

According to the procedure described in Example 2, starting with 1.7 g (7.79 mmol) of [(1-methyl-2-azepanyl)phenyl) methyl]amine, 1.49 g (7.79 mmol) of 1-[3-(dimethylamino) propyl]-3-ethylcarbodiimide hydrochloride, 1.05 g (7.79 mmol) of hydroxybenzotriazole and 1.74 g (7.79 mmol) of 2-chloro-3-trifluorobenzoic acid, and after work-up and purification by chromatography on silica gel, 0.8 g of erythro-2-chloro-N-(1-methyl-2-azepanyl)(phenyl)methyl]-3-(trifluoromethyl)benzamide is obtained.

This product is dissolved in a few ml of 2-propanol, 20 ml of a 0.1N solution of hydrogen chloride in 2-propanol are added and the mixture is concentrated under reduced pressure in order to reduce the volume of the solvent. After trituration, 0.48 g of hydrochloride is finally isolated in the form of a solid.

Melting point: 124-126° C.

Table 1 below illustrates the chemical structures and the melting points of a number of compounds of the invention. In the "salt" column, "-" denotes a compound in base form, "HCl" denotes a hydrochloride and "tfa" denotes a trifluoroacetate.

Compound 7 exists in the form of a mixture of erythro (7.5) and threo (2.5).

TABLE 1

(I)

[Structure: pyrrolidine with N-R₁, 2-position bearing (CH₂)ₙ linked to C1 with phenyl-X and HN-C(=O)-phenyl-R₂]

| No. | Stereochemistry | R₁ | n | X | R₂ | Salt | m.p. (° C.) |
|---|---|---|---|---|---|---|---|
| 1 | threo (1R, 2R; 1S, 2S) | CH₃ | 1 | H | 2-Cl, 3-CF₃ | HCl | 96-110 |
| 2 | threo (1R, 2R; 1S, 2S) | CH₃ | 1 | H | 2,6-Cl₂, 4-NH₂ | HCl | 155-162 |
| 3 | threo (1R, 2R; 1S, 2S) | allyl | 1 | H | 2-Cl, 3-CF₃ | — | 117-123 |
| 4 | threo (1S, 2S) | CH₃ | 1 | H | 4-Cl, 3-SO₂NH₂ | HCl | 165-170 |
| 5 | erythro (1R, 2S; 1S, 2R) | CH₃ | 1 | H | 3-Cl, 4-NH₂, 5-CF₃ | HCl | 130-140 |
| 6 | erythro (1R, 2S) | CH₃ | 1 | H | 4-Cl, 3-SO₂NH₂ | HCl | 190-192 |
| 7 | erythro (1R, 2S; 1S, 2R) | CH₃ | 3 | H | 2-Cl, 3-CF₃ | HCl | 124-126 |

The compounds of the invention were subjected to a series of pharmacological tests that demonstrated their value as therapeutically active substances.

Study of Glycine Transportation in SK-N-MC Cells Expressing the Native Human transporter glyt1

The uptake of [¹⁴C]glycine is studied in SK-N-MC cells (human neuroepithelial cells) expressing the native human transporter glyt1 by measuring the radioactivity incorporated in the presence or absence of the test compound. The cells are cultured as a monolayer for 48 hours in plates pretreated with 0.02% fibronectin. 10 On the day of the experiment, the culture medium is removed and the cells are washed with Krebs-HEPES buffer ([4-(2-hydroxyethyl)-1-piperazineethanesulfonic acid) at pH 7.4. After preincubation for 10 minutes at 37° C. in the presence either of buffer (control batch) or of test compound at various concentrations or of 10 mM glycine (determination of the nonspecific uptake), 10 µM of [¹⁴C]glycine (specific activity 112 mCi/mmol) are then added. Incubation is continued for 10 minutes at 37° C., and the reaction is quenched by washing twice with pH 7.4 Krebs-HEPES buffer. The radioactivity incorporated by the cells is then estimated after adding 100 µl of liquid scintillant and stirring for 1 hour. Counting is performed on a Microbeta Tri-Lux™ counter. The efficacy of the compound is determined by means of the IC$_{50}$, which is the concentration of compound that reduces by 50% the specific uptake of glycine, defined by the difference in radioactivity incorporated by the control batch and the batch that received 10 mM of glycine.

The compounds of the invention have an IC$_{50}$ in this test of about from 0.01 to 10 µM.

Study of the Glycine Transportation in Mouse Spinal Cord Homogenate

The uptake of [¹⁴C]glycine by the transporter glyt2 is studied in mouse spinal cord homogenate by measuring the radioactivity incorporated in the presence or absence of test compound.

After euthanizing the animals (male OF1 Iffa Credo mice weighing 20 to 25 g on the day of the experiment), the spinal cord of each animal is rapidly removed, weighed and stored on ice. The samples are homogenized in pH 7.4 Krebs-HEPES buffer ([4-(2-hydroxyethyl)-1-piperazineethanesulfonic acid), in a proportion of 25 ml/g of tissue.

50 µl of homogenate are preincubated for 10 minutes at 25° C. in the presence of pH 7.4 Krebs-HEPES buffer and of test compound at various concentrations, or of 10 mM of glycine to determine the nonspecific uptake. [¹⁴C]glycine (specific activity=112 mCi/mmol) is then added over 10 minutes at 25° C. to a final concentration of 10 µM. The reaction is quenched by vacuum filtration and the radioactivity is estimated by solid scintillation by counting on a Microbeta Tri-Lux counter. The efficacy of the compound is determined by means of the IC$_{50}$, the concentration capable of reducing by 50% the specific uptake of glycine, defined by the difference in radioactivity incorporated by the control batch and the batch that received 10 mM of glycine.

The compounds of the invention have an IC$_{50}$ in this test of about from 0.1 to 10 µM.

The results of the tests performed on the compounds of the invention show that they are inhibitors of the glycine transporter glyt1 present in the brain and glyt2 present in the spinal cord.

These results suggest that the compounds of the invention may be used for treating behavioral disorders associated with dementia, psychosis, in particular schizophrenia (deficient form and productive form) and acute or chronic extrapyramidal symptoms induced by neuroleptics, for the treatment of various forms of anxiety, panic attacks, phobia, compulsive obsessive disorders, for treating various forms of depression, including psychotic depression, for treating disorders caused by alcohol abuse or weaning from alcohol, sexual behavior disorders, eating disorders and for treating migraine.

Moreover, the compounds of the invention may be used for treating painful muscle contracture in rheumatology and in acute spinal pathology, for treating spastic con tractures of medullary or cerebral origin, for the symptomatic treatment of acute and subacute pain of light to moderate intensity, for treating intense and/or chronic pain, neurogenic pain and intractable pain, for treating Parkinson's disease and Parkinson-like symptoms of neurodegenerative origin or induced by neuroleptics, for treating partial primary and secondary generalized epilepsy of simple or complex symptomology, mixed forms and other epileptic syndromes in addition to another antiepileptic treatment, or in monotherapy, for the treatment of sleep apnea, and for neuroprotection.

Accordingly, a subject of the present invention is also pharmaceutical compositions containing an effective dose of at least one compound according to the invention, in the form of base or of pharmaceutically acceptable salt or solvate, and as a mixture, where appropriate, with suitable excipients.

Said excipients are chosen according to the pharmaceutical form and the desired mode of administration.

The pharmaceutical compositions according to the invention may thus be intended for oral, sublingual, subcutaneous, intramuscular, intravenous, topical, intra-tracheal, intranasal, transdermal, rectal or intraocular administration.

The unit administration forms may be, for example, tablets, gel capsules, granules, powders, oral or injectable solutions or suspensions, transdermal patches or suppositories. Pomades, lotions and eye drops may be envisioned for topical administration.

Said unit forms are dosed to allow a daily administration of from 0.01 to 20 mg of active principle per kg of body weight, according to the galenical form.

To prepare tablets, a pharmaceutical vehicle, which may be composed of diluents, for instance lactose, microcrystalline cellulose or starch, and formulating adjuvants, for instance binders (polyvinylpyrrolidone, hydroxypropylmethylcellulose, etc.), glidants, for instance silica, and lubricants, for instance magnesium stearate, stearic acid, glyceryl tribehenate or sodium stearylfumarate, are added to the micronized or nonmicronized active principle.

Wetting agents or surfactants such as sodium lauryl sulfate may also be added.

The preparation techniques may be direct tableting, dry granulation, wet granulation or hot melting.

The tablets may be plain, sugar-coated, for example coated with sucrose, or coated with various polymers or other suitable materials. They may be designed to allow rapid, delayed or sustained release of the active principle by means of polymer matrices or specific polymers used in the coating.

To prepare gel capsules, the active principle is mixed with dry pharmaceutical vehicles (simple mixing, dry or wet granulation, or hot melting), liquid or semisolid pharmaceutical vehicles.

The gel capsules may be hard or soft, with or without a film coating, so as to have rapid, sustained or delayed activity (for example for an enteric form).

A composition in the form of a syrup or elixir or for administration in the form of drops may contain the active principle together with a sweetener, preferably a calorie-free sweetener, methylparaben or propylparaben as antiseptic, a flavoring and a dye.

The water-dispersible powders and granules may contain the active principle as a mixture with dispersants or wetting agents, or dispersants such as polyvinyl-pyrrolidone, and also with sweeteners and flavor enhancers.

For rectal administration, use is made of suppositories prepared with binders that melt at the rectal temperature, for example cocoa butter or polyethylene glycols.

Aqueous suspensions, isotonic saline solutions or injectable sterile solutions containing pharmacologically compatible dispersants and/or wetting agents, for example propylene glycol or butylene glycol, are used for parenteral administration.

The active principle may also be formulated in the form of microcapsules, optionally with one or more supports or additives, or alternatively with a polymer matrix or with a cyclodextrin (transdermal patches, sustained-released forms).

The topical compositions according to the invention comprise a medium that is compatible with the skin. They may especially be in the form of aqueous, alcoholic or aqueous-alcoholic solutions, gels, water-in-oil or oil-in-water emulsions having the appearance of a cream or a gel, microemulsions or aerosols, or alternatively in the form of vesicular dispersions containing ionic and/or nonionic lipids. These galenical forms are prepared according to the usual methods of the fields under consideration.

Finally, the pharmaceutical compositions according to the invention may contain, along with a compound of general formula (I), other active principles that may be useful in the treatment of the disorders and diseases indicated above.

The invention claimed is:

1. A method of treating a behavioral disorder selected from psychoses, anxiety, and depression, which comprises administering to a patient with said disorder an effective amount of a compound of formula (I)

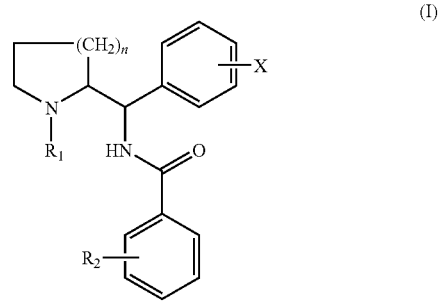

in which
n represents the number 1 or 3,
$R_1$ represents either a hydrogen atom, a linear or branched $(C_1-C_7)$alkyl group optionally substituted with one or more fluorine atoms, a $(C_3-C_7)$cycloalkyl group, a $(C_3-C_7)$cycloalkyl$(C_1-C_3)$alkyl group, a phenyl$(C_1-C_3)$alkyl group optionally substituted with one or two methoxy groups, a $(C_2-C_4)$alkenyl group, or a $(C_2-C_4)$alkynyl group,
X represents either a hydrogen atom or one or more substituents chosen from halogen atoms and trifluoromethyl and linear or branched $(C_1-C_6)$alkyl and $(C_1-C_6)$alkoxy groups,
$R_2$ represents either a hydrogen atom or one or more substituents chosen from halogen atoms and trifluoromethyl, linear or branched $(C_1-C_6)$alkyl and $(C_1-C_6)$alkoxy, $(C_3-C_7)$cycloalkyl, phenyl, cyano, acetyl, benzoyl, S$(C_1-C_6)$alkyl, $(C_1-C_6)$alkylsulfonyl, carboxyl and $(C_1-C_6)$alkoxycarbonyl groups, or a group of general formula $NR_3R_4$, $SO_2NR_3R_4$ or $CONR_3R_4$, in which $R_3$ and $R_4$ represent, independently of each other, a hydrogen atom or a linear or branched $(C_1-C_6)$alkyl or (C₃-C₇)cycloalkyl group, or form, with the nitrogen atom that bears them, a pyrrolidine, piperidine or morpholine ring, in the form of base or of acid-addition salt.

2. A compound selected from the group consisting of threo-2-chloro-N-[(1-methyl-2-pyrrolidinyl)phenylmethyl]-3-trifluoromethylbenzamide hydrochloride 1:1, threo-4-amino-3,5-dichloro-N—[(1-methyl-2-pyrrolidinyl)phenylmethyl) benzamide hydrochloride 1:1, threo-N-[(1-allyl-2-pyrrolidinyl)phenylmethyl]-2-chloro-3-trifluoromethylbenzamide 1:1,3-(Aminosulfonyl)-4-chloro-N-[(S)-[(2S)-1-methyl-2-pyrrolidinyl](phenyl)methyl]benzamide hydrochloride 1:1, erythro-4-amino-3-chloro-N-[1-methyl-2-pyrrolidinyl](phenyl)methyl]-5-(trifluoromethyl)benzamide hydrochloride 1:1,3-(Aminosulfonyl)-4-chloro-N-[(R)-[(2S)-1-methyl-2-pyrrolidinyl](phenyl)methyl]benzamide hydrochloride 1:1, and erythro-2-chloro-N-[(R)-[(2S)-1-methyl-2-azepanyl](phenyl)methyl]-3-(trifluoromethyl)benzamide hydrochloride 1:1.

3. A compound selected from the group consisting of threo-2-chloro-N-[(1-methyl-2-pyrrolidinyl)phenylmethyl]-3-trifluoromethylbenzamide; threo-4-amino-3,5-dichloro-N-[(1-methyl-2-pyrrolidinyl)phenylmethyl)benzamide; 3-(aminosulfonyl)-4-chloro-N-[(S) -[(2S)-1-methyl-2-pyrrolidinyl](phenyl)methyl]benzamide; erythro-4-amino-3-chloro-N-[1-methyl-2-pyrrolidinyl](phenyl)methyl]-5-(trifluoromethyl)benzamide; 3-(aminosulfonyl)-4-chloro-N-[(R)-[(2S)-1-methyl-2-pyrrolidinyl](phenyl)methyl] benzamide; and erythro-2-chloro-N-[(R)-[(2S)-1-methyl-2-azepanyl](phenyl)methyl]-3-(trifluoromethyl)benzamide, or a pharmaceutically acceptable salt thereof.

4. The method according to claim 1, wherein the compound is selected from the group consisting of threo-2-chloro-N-[(1-methyl-2-pyrrolidinyl)phenylmethyl]-3-trifluoromethylbenzamide; threo-4-amino-3,5-dichloro-N-[(1-methyl-2-pyrrolidinyl) -phenylmethyl)benzamide; threo-N-[(1-allyl-2-pyrrolidinyl)phenylmethyl]-2-chloro-3-trifluoromethylbenzamide; 3-(aminosulfonyl)-4-chloro-N-[(S)-[(2S)-1-methyl-2-pyrrolidinyl](phenyl)methyl] benzamide; erythro-4-amino-3-chloro-N-[1-methyl-2-pyrrolidinyl](phenyl)methyl]-5-(trifluoromethyl) benzamide; 3-(aminosulfonyl)-4-chloro-N-[(R)-[(2S)-1-methyl-2-pyrrolidinyl](phenyl)methyl]benzamide; and erythro-2-chloro-N-[(R)-[(2S)-1-methyl-2-azepanyl](phenyl)methyl]-3-(trifluoromethyl)benzamide; or a pharmaceutically acceptable salt thereof.

* * * * *

UNITED STATES PATENT AND TRADEMARK OFFICE
CERTIFICATE OF CORRECTION

PATENT NO.        : 7,700,585 B2
APPLICATION NO.   : 11/741803
DATED             : April 20, 2010
INVENTOR(S)       : Gihad Dargazanli et al.

It is certified that error appears in the above-identified patent and that said Letters Patent is hereby corrected as shown below:

On the Title page, in field (75), in column 1, in "Inventors", line 5, delete "Longiumeau" and insert -- Longjumeau --, therefor.

On page 2, in column 1, under "Other Publications" item (56), line 12, delete "(2005)" and insert -- (2006) --, therefor.

In column 3-4, in 5<sup>th</sup> Structure, delete " " insert -- 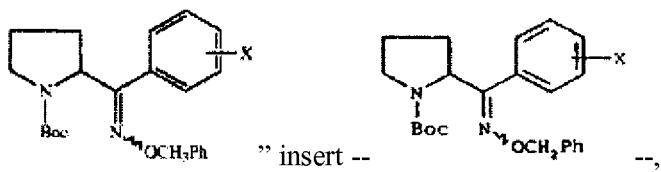 --, therefor.

In column 3-4, in 8<sup>th</sup> Structure, delete " 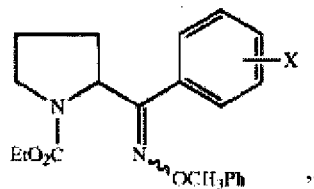 " insert

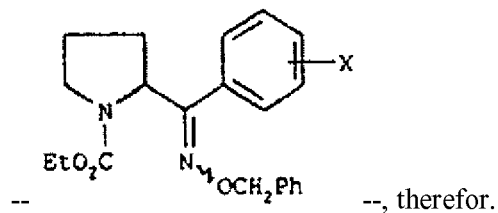 --, therefor.

Signed and Sealed this
Fifth Day of April, 2011

David J. Kappos
*Director of the United States Patent and Trademark Office*

In column 3-4, in 7th Structure, delete " 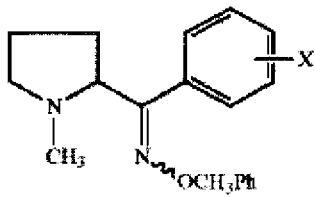 " insert

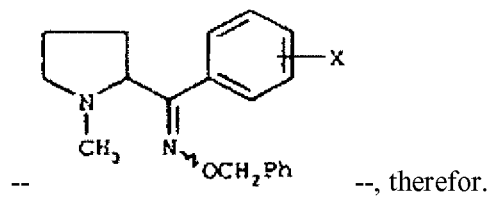 --, therefor.

In column 10, line 30-31, delete "methylpyrolidinyl" and insert -- methylpyrrolidinyl --, therefor.

In column 13, line 17, delete "IN" and insert -- -1N --, therefor.

In column 13, line 39, delete "mol" and insert -- mmol --, therefor.

In column 14, line 54, delete "pyrrolidinyl] (phenyl)" and insert -- pyrrolidinyl](phenyl) --, therefor.

In column 17, line 41, before "On" delete "10".

In column 18, line 45, delete "Tri-Lux" and insert -- Tri-Lux™ --, therefor.